United States Patent
Rivers et al.

(10) Patent No.: US 7,662,970 B2
(45) Date of Patent: *Feb. 16, 2010

(54) OXAZOLIDINIUM COMPOUNDS AND USE AS HYDRATE INHIBITORS

(75) Inventors: Gordon T. Rivers, Houston, TX (US); Jun Tian, League City, TX (US); James A. Hackerott, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 11 days.

This patent is subject to a terminal disclaimer.

(21) Appl. No.: 11/872,887

(22) Filed: Oct. 16, 2007

(65) Prior Publication Data

US 2008/0119656 A1 May 22, 2008

Related U.S. Application Data

(60) Provisional application No. 60/866,253, filed on Nov. 17, 2006.

(51) Int. Cl.
*C07D 263/04* (2006.01)

(52) U.S. Cl. ...................... 548/215; 585/899

(58) Field of Classification Search ................. 548/215; 585/899

See application file for complete search history.

(56) References Cited

U.S. PATENT DOCUMENTS

| 4,480,126 | A | 10/1984 | Rutzen |
| 5,110,585 | A | 5/1992 | Chaudhuri et al. |
| 5,132,377 | A | 7/1992 | Nakano et al. |
| 5,427,774 | A | 6/1995 | Chaudhuri et al. |
| 7,164,051 | B2 * | 1/2007 | Rivers et al. ................. 585/15 |
| 2004/0110998 | A1 * | 6/2004 | Rivers et al. ................. 585/15 |

OTHER PUBLICATIONS

Ager et al. (Chem. Rev., 1996, 96(2); 835-876).*
N. J. Leonard, et al., "Small Charged Rings. IV. Expansion of the Aziridinium Ring by Reaction with Aldehydes," Journal of Organic Chemistry, Oct. 1963, pp. 2850-2854, vol. 28.

* cited by examiner

*Primary Examiner*—Kamal A Saeed
*Assistant Examiner*—Valerie Rodriguez-Garcia
(74) *Attorney, Agent, or Firm*—Mossman Kumar & Tyler PC

(57) ABSTRACT

Oxazolidinium compounds are formed by the reaction of a halohydrin or an epoxide with a secondary amine and an aldehyde or a ketone. The oxazolidinium compounds are formed directly and do not require the reaction of a pre-formed oxazolidine with an alkylating agent. The compounds are useful as gas hydrate inhibitors in oil and gas production and transportation.

12 Claims, No Drawings

OXAZOLIDINIUM COMPOUNDS AND USE AS HYDRATE INHIBITORS

CROSS-REFERENCE TO RELATED APPLICATION

This application claims the benefit of U.S. Provisional Patent Application No. 60/866,253 filed Nov. 17, 2006.

TECHNICAL FIELD

The invention relates to oxazolidinium compounds and methods for making them, and most particularly relates, in one non-limiting embodiment, to oxazolidinium compounds useful for inhibiting the formation of hydrocarbon hydrates during the production of oil and gas, and direct methods for making such oxazolidinium compounds.

BACKGROUND

A number of hydrocarbons, especially lower-boiling light hydrocarbons, in formation fluids or natural gas are known to form hydrates in conjunction with the water present in the system under a variety of conditions—particularly at the combination of lower temperature and higher pressure. The hydrates usually exist in solid forms that are essentially insoluble in the fluid itself. As a result, any solids in a formation or natural gas fluid are at least a nuisance for production, handling and transport of these fluids. It is not uncommon for hydrate solids (or crystals) to cause plugging and/or blockage of pipelines or transfer lines or other conduits, valves and/or safety devices and/or other equipment, resulting in shutdown, loss of production and risk of explosion or unintended release of hydrocarbons into the environment either on-land or off-shore. Accordingly, hydrocarbon hydrates have been of substantial interest as well as concern to many industries, particularly the petroleum and natural gas industries.

Hydrocarbon hydrates are clathrates, and are also referred to as inclusion compounds. Clathrates are cage structures formed between a host molecule and a guest molecule. A hydrocarbon hydrate generally is composed of crystals formed by water host molecules surrounding the hydrocarbon guest molecules. The smaller or lower-boiling hydrocarbon molecules, particularly $C_1$ (methane) to $C_4$ hydrocarbons and their mixtures, are more problematic because it is believed that their hydrate or clathrate crystals are easier to form. For instance, it is possible for ethane to form hydrates at as high as 4° C. at a pressure of about 1 MPa. If the pressure is about 3 MPa, ethane hydrates can form at as high a temperature as 14° C. Even certain non-hydrocarbons such as carbon dioxide, nitrogen and hydrogen sulfide are known to form hydrates under certain conditions.

There are two broad techniques to overcome or control the hydrocarbon hydrate problems, namely thermodynamic and kinetic. For the thermodynamic approach, there are a number of reported or attempted methods, including water removal, increasing temperature, decreasing pressure, addition of "antifreeze" to the fluid and/or a combination of these. The kinetic approach generally attempts (a) to prevent the smaller hydrocarbon hydrate crystals from agglomerating into larger ones (known in the industry as an anti-agglomerate and abbreviated AA) and/or (b) to inhibit and/or retard initial hydrocarbon hydrate crystal nucleation; and/or crystal growth (known in the industry as a kinetic hydrate inhibitor and abbreviated KHI). Thermodynamic and kinetic hydrate control methods may be used in conjunction.

Kinetic efforts to control hydrates have included use of different materials as inhibitors. For instance, onium compounds with at least four carbon substituents are used to inhibit the plugging of conduits by gas hydrates. Additives such as polymers with lactam rings have also been employed to control clathrate hydrates in fluid systems. These kinetic inhibitors are commonly labeled Low Dosage Hydrate Inhibitors (LDHI) in the art. KHIs and even LDHIs are relatively expensive materials, and it is always advantageous to determine ways of lowering the usage levels of these hydrate inhibitors while maintaining effective hydrate inhibition.

Thus, it is desirable if new gas hydrate inhibitors were discovered which would yield comparable or improved results over known gas hydrate inhibitors, and it is also desirable to find new ways of forming gas hydrate inhibitors.

Oxazolidinium compounds are generally known in the art. They are known to be formed by ring expansion of aziridinium compounds (N.J. Leonard, et al., *Journal of Organic Chemistry*, Vol. 28, p. 2850+ (1963)), and also by the alkylation of preformed oxazolidines (U.S. Pat. No. 5,427,774 to R. K. Chaudhuri, et al. and U.S. Pat. No. 5,132,377 to S. Nakano, et al.). More direct methods of forming oxazolidinium compounds are not known.

SUMMARY

There is provided, in one form, a method for preparing an oxazolidinium compound that involves reacting an aldehyde and/or a ketone with a secondary amine and a halohydrin and/or an epoxide under reaction conditions sufficient to produce an oxazolidinium compound.

In another non-limiting embodiment herein, there is provided an oxazolidinium compound prepared by a method that involves reacting an aldehyde and/or a ketone with a secondary amine and a halohydrin and/or an epoxide, under reaction conditions sufficient to produce an oxazolidinium compound. The oxazolidinium compound may have the structure:

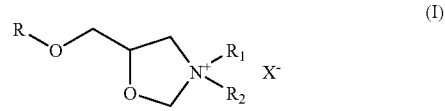

(I)

where R is a hydrocarbon substituent containing from 1 to 20 carbon atoms, and may be optionally substituted with heteroatoms such as oxygen, nitrogen, phosphorus and combinations thereof. $R_1$ and $R_2$ each independently have 1 to 20 carbon atoms, may be linear, branched or cyclic and may be optionally substituted with alkyl groups, aryl groups, alkylaryl groups, and aryl groups substituted with alkoxy groups. X is chlorine, fluorine, bromine and/or iodine.

In a different non-restrictive embodiment, there is presented a method for inhibiting formation of hydrocarbon hydrates that involves contacting a fluid containing a mixture of water and hydrate-forming guest molecules at gas hydrate forming conditions with an amount of oxazolidinium compound effective to inhibit formation of hydrocarbon hydrates at the conditions. The oxazolidinium compound is prepared by a method involving reacting an aldehyde and/or a ketone with a secondary amine and a reactant that is a halohydrin and/or an epoxide, under reaction conditions sufficient to produce an oxazolidinium compound. Alternatively or in addition thereto, the oxazolidinium compound may have the structure (I) above.

DETAILED DESCRIPTION

In the present invention there are included methods and compositions used herein for inhibiting, retarding, mitigating, reducing, controlling and/or delaying formation of hydrocarbon hydrates or agglomerates of hydrates in fluids used in hydrocarbon recovery operations. The method may be applied to prevent or reduce or mitigate plugging of annular spaces, pipes, transfer lines, valves, and other places or equipment downhole where hydrocarbon hydrate solids may form under conditions conducive to their formation or agglomeration.

The term "inhibiting" is used herein in a broad and general sense to mean any improvement in preventing, controlling, delaying, abating, reducing or mitigating the formation, growth and/or agglomeration of hydrocarbon hydrates, particularly light hydrocarbon gas hydrates in any manner, including, but not limited to kinetically, thermodynamically, by dissolution, by breaking up, by anti-agglomeration other mechanisms, or any combination thereof. Although the term "inhibiting" is not intended to be restricted to the complete cessation of gas hydrate formation, it may include the possibility that formation of any gas hydrate is entirely prevented.

The terms "formation" or "forming" relating to hydrates are used herein in a broad and general manner to include, but are not limited to, any formation of hydrate solids from water and hydrocarbon(s) or hydrocarbon and non-hydrocarbon gas(es), growth of hydrate solids, agglomeration of hydrates, accumulation of hydrates on surfaces, any deterioration of hydrate solids plugging or other problems in a system and combinations thereof.

The present method is useful for inhibiting hydrate formation for many hydrocarbons particularly including hydrocarbon and non-hydrocarbon mixtures. The method is particularly useful for lighter or low-boiling, $C_1$-$C_5$, hydrocarbon gases, non-hydrocarbon gases or gas mixtures at ambient conditions. Examples of such gases include, but are not necessarily limited to, methane, ethane, ethylene, acetylene, propane, propylene, methylacetylene, n-butane, isobutane, 1-butene, trans-2-butene, cis-2-butene, isobutene, butene mixtures, isopentane, pentenes, natural gas, carbon dioxide, hydrogen sulfide, nitrogen, oxygen, argon, krypton, xenon, and mixtures thereof. These molecules are also termed hydrate-forming guest molecules herein. Other examples include various natural gas mixtures that are present in many gas and/or oil formations and natural gas liquids (NGL). The hydrates of all of these low-boiling hydrocarbons are also referred to as gas hydrates. The hydrocarbons may also comprise other compounds including, but not limited to CO, $CO_2$, COS, hydrogen, hydrogen sulfide ($H_2S$), and other compounds commonly found in gas/oil formations or processing plants, either naturally occurring or used in recovering/processing hydrocarbons from the formation or both, and mixtures thereof.

More specifically, the oxazolidinium compounds herein would be useful hydrate inhibitors in many fluids involved in hydrocarbon recovery operations including, but not limited to, drilling fluids, drill-in fluids, workover fluids, completion fluids and the like. Suitable salts for forming the brines of these fluids include, but are not necessarily limited to, sodium chloride, calcium chloride, zinc chloride, potassium chloride, potassium bromide, sodium bromide, calcium bromide, zinc bromide, sodium formate, potassium formate, ammonium formate, cesium formate, and mixtures thereof.

Suitable gas hydrate inhibitors for use in the methods and fluid compositions herein may include, but are not necessarily limited to, certain oxazolidinium compounds. The oxazolidinium compounds may have the structure:

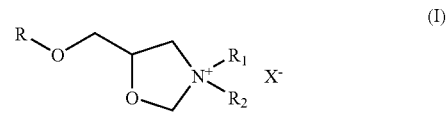

(I)

where R is a hydrocarbon substituent containing from 1 to 20 carbon atoms, and may be optionally substituted with heteroatoms selected from the group consisting of oxygen, nitrogen, phosphorus and combinations thereof; $R_1$ and $R_2$ each independently have 1 to 20 carbon atoms, and may be linear, branched or cyclic and may be optionally substituted with alkyl groups, aryl groups, alkylaryl groups, and aryl groups substituted with alkoxy groups. X may be chlorine, fluorine, bromine or iodine and combinations thereof. These oxazolidinium compounds are believed to be novel compositions of matter.

A particularly useful oxazolidinium compound falling within the definition of structure (I) above, in turn has the structure:

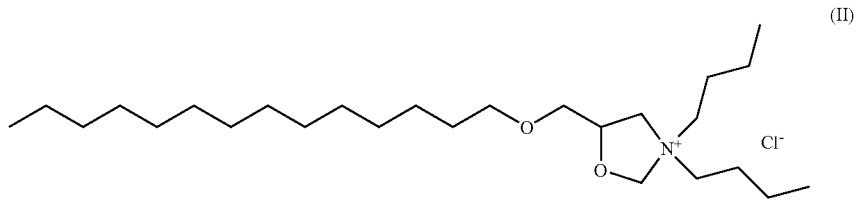

(II)

where R is a C14 linear alkyl (or may be C12 or a mixture of the two), $R_1$ and $R_2$ are each n-butyl substituents, and X is chlorine.

Generally, the oxazolidinium compounds are prepared by reacting an aldehyde and/or a ketone with a secondary amine and a halohydrin and/or an epoxide, under reaction conditions sufficient to produce an oxazolidinium compound. Suitable reaction conditions include a temperature ranging from about ambient to about 120° C., inclusive, and a pressure ranging from about ambient to the pressure required to keep the reactants and solvents in the liquid phase, inclusive. In an alternative, non-restrictive embodiment, the reaction temperature may range between ambient and about 90° C. The oxazolidinium compounds are formed directly and do not require the reaction of a pre-formed oxazolidine with an alkylating agent as in some prior preparation methods.

With respect to reactant proportions, in some cases, up to 10 mol equivalents of one or two reactants may be used. In other cases, up to 2 mol equivalents of one or two reactants may be used. However, the ideal reactant ratios are often one mol equivalent of halohydrin (or epoxide) with one mol equivalent of aldehyde (or ketone) with one mol equivalent of secondary amine.

In one non-limiting embodiment, a suitable aldehyde reactant is formaldehyde. Alternatively, the aldehyde may be one having 1 to 20 carbon atoms and the ketone may be one having 3 to 20 carbon atoms. Specific, suitable aldehydes may include, but are not necessarily limited to, formaldehyde, pivaldehyde (trimethylacetaldehyde) and/or benzaldehyde, and the like. Specific, suitable ketones may include, but are not necessarily limited to, acetone, butanone and/or acetophenone, and the like.

Suitable halohydrins for use herein may have the general formula:

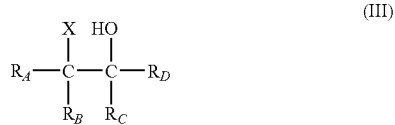

(III)

where X is chlorine, fluorine, bromine or iodine; and where $R_A$, $R_B$, $R_C$ and $R_D$ are each independently selected from the group consisting of hydrogen, hydrocarbon substituents containing from 1 to 20 carbon atoms, and heteroatoms selected from the group consisting of oxygen, nitrogen, phosphorus and combinations thereof. If $R_A$, $R_B$, $R_C$ and $R_D$ are heteroatoms, their remaining valences may be occupied with H atoms.

Suitable epoxides for use in the methods and compositions herein include, but are not necessarily limited to, glycidyl ether, phenyl glycidyl ether, bisphenol A diglycidyl ether, alkyl glycidyl ethers having 1 to 20 carbon atoms, epoxides of alpha olefins containing 2 to 20 carbon atoms, and the like.

Suitable secondary amines for forming the oxazolidinium compounds herein include those having 2 to 20 carbon atoms, and may be linear, branched or cyclic and may be substituted with alkyl groups, such as diethanolamine, aryl groups such as furfuryl or phenyl, alkylaryl groups such as benzyl, and/or aryl groups substituted with alkoxy groups such as paramethoxyphenyl. Suitable secondary cyclic amines include, but are not necessarily limited to compounds such as pyrrolidine or morpholine and the like.

The contacting of the oxazolidinium gas hydrate inhibitors herein with the mixture of hydrocarbon, water and hydrate-forming guest molecules may be achieved by a number of ways or techniques, including, but not necessarily limited to, mixing, blending with mechanical mixing equipment or devices, stationary mixing setup or equipment, magnetic mixing or other suitable methods, other equipment and means known to one skilled in the art and combinations thereof to provide adequate contact and/or dispersion of the composition in the mixture. The contacting can be made in-line or offline or both. The various components of the composition may be mixed prior to or during contact, or both. The oxazolidinium gas hydrate inhibitor should be prepared or formed prior to addition to the mixture or liquid that has potential for hydrate formation. If needed or desired, the oxazolidinium compound may be optionally removed or separated mechanically, chemically, or by other methods known to one skilled in the art, or by a combination of these methods after the hydrate formation conditions and/or hydrate-forming species are no longer present.

Because the present compositions and methods are particularly suitable for inhibiting hydrate formation by lower boiling hydrocarbons or hydrocarbon and/or non-hydrocarbon gases at ambient conditions with no more than five carbon atoms, the pressure of the hydrate-forming condition is usually at or greater than atmospheric pressure (i.e. greater than or equal to about 101 kPa), in one non-limiting embodiment greater than about 1 MPa, and in an alternate version greater than about 5 MPa. The pressure in certain formations or processing plants or units could be much higher, say greater than about 20 MPa. There is no specific high pressure limit. The present method can be used at any pressure that allows formation of hydrocarbon gas hydrates.

The temperature of the condition for contacting is usually below, the same as, or not much higher than the ambient or room temperature. Lower temperatures tend to favor hydrate formation, thus requiring the treatment with the present compositions. At much higher temperatures, however, hydrocarbon hydrates may not form, thus obviating the need of carrying out any treatments.

It will be appreciated that it may be difficult to predict in advance the proportions of oxazolidinium gas hydrate inhibitors herein effective in inhibiting hydrocarbon hydrate formations in a particular fluid any given situation. There are a number of complex, interrelated factors that must be taken into account in determining the effective dosage or proportion, including, but not necessarily limited to, the proportion of water in the fluid, the nature of the hydrocarbon, the nature of the hydrate-forming guest molecules, the temperature and pressure conditions that the mixture of hydrocarbon and water are subject to, the particular hydrocarbon hydrate inhibitor employed, etc. Experimentation with a particular set of conditions or in a specific system may be a suitable way to determine the optimum dosage range. Care should be taken to avoid the formation of problematic quantities of irreversible, harmful hydrate masses. Nevertheless, in the interest of attempting to provide some general guidance of effective proportions, relative to the water phase, the amount of the hydrate inhibitor is about 10 volume % or less, alternatively 8 volume % or less, and in another non-limiting embodiment is less than 6 vol %. In one non-limiting embodiment the lower limit is independently about 0.01 volume %, and alternatively is about 0.1 vol % and possibly is about 0.5 vol %.

In addition to the gas hydrate inhibitor herein, the hydrocarbon inhibitor composition and the fluid being treated may further comprise other additional components, including, but not limited to, different controlling chemistries such as corrosion inhibitors, wax inhibitors, scale inhibitors, asphaltene inhibitors and other gas hydrate inhibitors and/or solvents. Suitable solvents for the gas hydrate inhibitors herein may include, but are not limited to water; at least one oxygenated compound selected from $C_1$-$C_6$ alcohols, $C_2$-$C_6$ glycols, $C_1$-$C_6$ mono-aliphatic, in one non-limiting embodiment mono-alkyl, ethers of $C_2$-$C_6$ glycol, glycerin, $C_1$-$C_6$ mono-aliphatic, suitably mono-alkyl, ethers of glycerin, $C_1$-$C_6$ di-aliphatic, particularly dialkyl, ethers of glycerin, glycerin esters of $C_1$-$C_6$ carboxylate; N-methylpyrrolidone; sulfolane; $C_3$-$C_{10}$ ketones, and mixtures thereof. Examples of acceptable solvents in one non-limiting embodiment include water and liquid oxygenated materials such as methanol, ethanol, propanol, glycols like ethylene glycol, 1,2-propylene glycol, 1,3-propylene glycol, glycerin, esters and ethers of glycerin, CELLOSOLVE® (2-ethoxyethanol), CELLOSOLVE derivatives, 2-propoxyethanol, 2-isopropoxyethanol, 2-butoxyethanol, 2-isobutoxyethanol, 2-methoxyethanol, ethoxylated propylene glycols, ketones such as cyclohexanone and diisobutylketone, and mixtures thereof. The solvent is present in the total hydrocarbon hydrate inhibiting composition in the range of from 0 wt % to about 85 wt %, alternatively from about 0 wt % to about 65 wt %, of the total composition, based on volume. CELLOSOLVE is a registered trademark of Union Carbide Corporation.

Because some of the oxazolidinium gas hydrate inhibitor disclosed herein will be solids or gummy-like amorphous organic materials under ambient conditions, it is often helpful to use a suitable solvent as described above in the composition. This allows the formation of a homogeneous or uniform solution, suspension, emulsion or a combination of these, of all the components for easier mixing or distributing or dispersing the composition in the hydrocarbon/water fluid or system to be treated. As a result, more efficient and/or favorable contacting of the composition with the mixture comprising water and the hydrate-forming guest molecules may be effected.

The present invention also may be used in combination with other methods or processes, which have been known to one skilled in the art as discussed in the background to help inhibit formation of hydrates. The compositions and methods will now be further illustrated with respect to specific Examples which are intended to further illuminate the invention but not limit it in any way.

PREPARATORY EXAMPLE 1

In a 4 ounce (0.12 liter) vial were placed 9.01 g of a chlorohydrin derived from epichlorohydrin and ALFOL 1214 (trade name for a mixture of dodecyl and tetradecyl alcohols) 3.99 g of di-n-butylamine, 2.51 g of 37 aqueous formaldehyde and 4.00 g of methanol as a solvent. The vial was loosely capped with aluminum foil, sealed in a stainless steel pressure vessel, and pressurized to 150 psig (1.03 MPa) with nitrogen. The pressure vessel was placed in an oven at 120° C. for 20 hours. The pressure vessel was allowed to cool to room temperature and vented. The vial contained a clear water soluble amber liquid. NMR analysis confirmed the conversion of starting materials to an oxazolidinium compound.

HYDRATE INHIBITION EXAMPLES 2-5

The following components were tested for gas hydrate inhibition efficacy: RE4394—a current, commercial hydrate inhibitor product, and Composition A—a dilution of the inventive oxazolidinium compound of Example 1.

The various compositions were tested under the conditions shown in Table I. The liquid hydrocarbon used was from a proprietary location and known to have hydrate formation concerns at the test conditions. The following observations may be made:

At subcooling of 36° F. (2.2° C.), no hydrate morphology control was observed for RE 4394 and Composition A.

At subcooling of 25° F. (−3.9° C.), all three show hydrate control at low water cut.

The rankings are conducted on an A-F system where A is best and F is worst. LDHI refers to Low Dosage Hydrate Inhibitors; LH refers to "liquid height".

TABLE I

Gas Hydrate Inhibitor Testing
Goals: Test RE 4394 & Composition A
Target: 1300 psig (8.96 MPa) @ 40° F. (9.4° C.)

| | Cell | | | |
|---|---|---|---|---|
| | 2 | 3 | 4 | 5 |
| LDHI | RE 4394 @ 2.5 Vol % | Comp. A @ 2.5 Vol % | RE 4394 @ 1.5 Vol % | Comp. A @ 1.5 Vol % |
| Liquid Hydrocarbon Phase | 50 vol % | 50 vol % | 75 vol % | 75 vol % |
| Gas Phase | 15/85 Propane/Methane | 15/85 Propane/Methane | 15/85 Propane/Methane | 15/85 Propane/Methane |
| Brine | DI Water, 6 mL | DI Water, 6 mL | DI Water, 3 mL | DI Water, 3 mL |
| Observations before cool-down | Condensate is slightly turbid; Upon contact brine being transparent; Little small crystal observed on the wall even at RT for short time | Condensate is slightly turbid; Unable to determine the clarity of brine, but only slightly turbid at worst; Fine whitish layer at liquid interface | Condensate is slightly turbid; Unable to determine the clarity of brine, but only slightly turbid at worst; Fine whitish layer at liquid interface | Condensate is slightly turbid; Unable to determine the clarity of brine, but only slightly turbid at worst; Fine whitish layer at liquid interface |
| LH (mm) | >32 | >32 | >32 | >32 |
| | Chiller Temperature 1.5° C. - Bath Temperature 37° F. (2.8° C.) | | | |
| Observations @ 16.00 hr | Large chunk of hydrates adhering to cell's interior, and block ball move; Little condensates observed | Large chunk of hydrates adhering to cell's interior, and block ball move; Little condensates observed | Large chunk of hydrates adhering to cell's interior, and block ball move; Little condensates observed | Large chunk of hydrates adhering to cell's interior, and block ball move; Little condensates observed |
| LH (mm) | n/a | n/a | n/a | n/a |
| Ranking | F | F | F | F |
| | Chiller Temperature 5° C. - Bath Temperature 42° F. (5.6° C.) | | | |
| Observations @ 40 hr | Large chunk of hydrates adhering to cell's interior, and block ball move; Little condensates observed | Large chunk of hydrates adhering to cell's interior, and block ball move; Little condensates observed | Large chunk of hydrates adhering to cell's interior, and block ball move; Little condensates observed | Large chunk of hydrates adhering to cell's interior, and block ball move; Little condensates observed |

TABLE I-continued

Gas Hydrate Inhibitor Testing
Goals: Test RE 4394 & Composition A
Target: 1300 psig (8.96 MPa) @ 40° F. (9.4° C.)

| | Cell | | | |
|---|---|---|---|---|
| | 2 | 3 | 4 | 5 |
| LH (mm) | n/a | n/a | n/a | n/a |
| Ranking | F | F | F | F |
| | | Chiller Temperature 8.5° C. - Bath Temperature 48° F. (8.9° C.) | | |
| Observations @ 48 hr | Large chunk of hydrates adhering to cell's interior, and block ball move; Little condensates observed | Dispersion of tiny hydrates in condensate and water; Both balls rock with ease; Clear two phase observed. | Dispersion of tiny hydrates in condensate and water; Both balls rock with ease; Clear two phase observed. | Dispersion of tiny hydrates in condensate and water; Both balls rock with ease; Clear two phase observed. |
| LH (mm) | n/a | >32 | >32 | >32 |
| Ranking | F | B | A | A |

PREPARATORY EXAMPLE 6

The inventive oxazolidinium compounds may be made from an epoxide by a procedure such as the following. In a 2 ounce bottle (0.06 liter) were placed 3.95 gm Heloxy® 8 (trade name for a C12/C14 glycidyl ether of approximate 85% purity), 1.06 gm of 37% aqueous formaldehyde, 1.69 gm of di-n-butylamine, 1.29 gm of 37% aqueous hydrochloric acid, and 2.00 gm of methanol. The bottle was capped and placed in an oven at 60° C. for 18 hours. The bottle was cooled to room temperature and contained a clear water soluble amber liquid. NMR analysis confirmed the conversion of starting materials to the same oxazolidinium compound as that made in Example 1.

PREPARATORY EXAMPLE 7

Example 1 was repeated at an oven temperature of 90° C. for 14 hours with a similar conversion to the same oxazolidinium compound.

Many modifications may be made in the compositions and methods of this invention without departing from the spirit and scope thereof that are defined only in the appended claims. For example, the exact oxazolidinium compounds may be different from those explicitly mentioned herein. Various combinations of gas hydrate inhibitors alone or together other than those described here are also expected to be useful. Further, oxazolidinium compounds used alone or together with mixtures of water, hydrocarbons and hydrate-forming guest molecules different from those exemplified herein would be expected to be successful within the context of this invention. Additionally, preparatory methods different than those exemplified herein with respect to reactants and reaction conditions but nevertheless falling within the boundaries of the inventive method are still included. For instance, different aldehydes, ketones, secondary amines, halohydrins and epoxides from those explicitly mentioned herein may be used, and further, reaction conditions different from those exemplified and specifically mentioned are also expected to be useful.

What is claimed is:

1. A method for inhibiting formation of hydrates comprising contacting a fluid including a mixture comprising water and hydrate-forming guest molecules at gas hydrate forming conditions with an amount of a mixture of oxazolidinium compounds effective to inhibit formation of hydrocarbon hydrates at the gas hydrate forming conditions, where the mixture of oxazolidinium compounds is prepared by a method comprising reacting an aldehyde and/or a ketone with a secondary amine and a reactant selected from the group consisting of a halohydrin and an epoxide, under reaction conditions sufficient to produce the mixture of oxazolidinium compounds, where the hydrate-forming guest molecules are selected from the group consisting of methane, ethane, ethylene, acetylene, propane, propylene, methylacetylene, n-butane, isobutane, 1-butene, trans-2-butene, cis-2-butene, isobutene, butene mixtures, isopentane, pentenes, natural gas, carbon dioxide, hydrogen sulfide, nitrogen, oxygen, argon, krypton, xenon, and mixtures thereof.

2. The method of claim 1 where the amount of the mixture of oxazolidinium compounds in the fluid ranges from about 0.01 to about 10 volume % based on the water present.

3. The method of claim 1 where the aldehyde has from 1 to 20 carbon atoms and the ketone has from 3 to 20 carbon atoms.

4. The method of claim 1 where the halohydrin has the formula

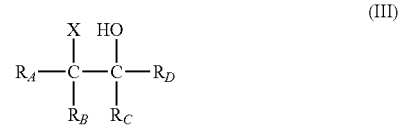

(III)

wherein X is selected from the group consisting of chlorine, fluorine, bromine or iodine; and wherein $R_A$, $R_B$, $R_C$ and $R_D$ are each independently selected from the group consisting of hydrogen, hydrocarbon substituents containing from 1 to 20 carbon atoms, and heteroatoms selected from the group consisting of oxygen, nitrogen, phosphorus and combinations thereof.

5. The method of claim 1 where the secondary amine has from 2 to 20 carbon atoms, may be linear, branched or cyclic and may be substituted with alkyl groups, aryl groups, alkylaryl groups, and aryl groups substituted with alkoxy groups.

6. The method of claim 1 where the reaction conditions comprise a temperature ranging from about ambient to about 120° C., and a pressure ranging from about ambient to that required to keep the reactants and solvents in the liquid phase.

7. The method of claim 1 where the reacting is conducted with formaldehyde and where at least one oxazolidinium compound in the mixture has the formula:

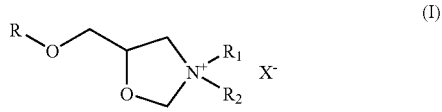

where R is a hydrocarbon substituent containing from 1 to 20 carbon atoms, a hydrocarbon substituent containing from 1 to 20 carbon atoms substituted with a heteroatom selected from the group consisting of oxygen, nitrogen, phosphorus and combinations thereof; $R_1$ and $R_2$ each independently have 1 to 20 carbon atoms, may be linear, branched or cyclic; linear, branched or cyclic groups having 1 to 20 carbon atoms substituted with alkyl groups, aryl groups, alkylaryl groups, and aryl groups substituted with alkoxy groups, and X is selected from the group consisting of chlorine, fluorine, bromine or iodine.

8. A method for inhibiting formation of hydrates comprising contacting a fluid including a mixture comprising water and hydrate-forming guest molecules at gas hydrate forming conditions with from about 0.01 to about 10 volume % of a mixture of oxazolidinium compounds, based on the water present, where the mixture of oxazolidinium compounds is prepared by a method comprising reacting formaldehyde with a secondary amine and a reactant selected from the group consisting of a halohydrin and an epoxide, under reaction conditions sufficient to produce an oxazolidinium compound having the formula:

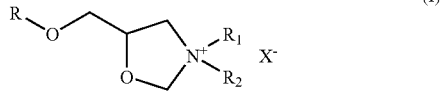

where R is a hydrocarbon substituent containing from 1 to 20 carbon atoms, a hydrocarbon substituent containing from 1 to 20 carbon atoms substituted with a heteroatom selected from the group consisting of oxygen, nitrogen, phosphorus and combinations thereof; $R_1$ and $R_2$ each independently have 1 to 20 carbon atoms, may be linear, branched or cyclic; linear, branched or cyclic groups having 1 to 20 carbon atoms substituted with alkyl groups, aryl groups, alkylaryl groups, and aryl groups substituted with alkoxy groups, and X is selected from the group consisting of chlorine, fluorine, bromine or iodine, where the hydrate-forming guest molecules are selected from the group consisting of methane, ethane, ethylene, acetylene, propane, propylene, methylacetylene, n-butane, isobutane, 1-butene, trans-2-butene, cis-2-butene, isobutene, butene mixtures, isopentane, pentenes, natural gas, carbon dioxide, hydrogen sulfide, nitrogen, oxygen, argon, krypton, xenon, and mixtures thereof.

9. The method of claim 8 where the aldehyde has from 1 to 20 carbon atoms and the ketone has from 3 to 20 carbon atoms.

10. The method of claim 8 where the halohydrin has the formula

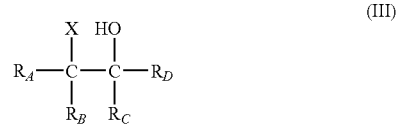

wherein X is selected from the group consisting of chlorine, fluorine, bromine or iodine; and wherein $R_A$, $R_B$, $R_C$ and $R_D$ are each independently selected from the group consisting of hydrogen, hydrocarbon substituents containing from 1 to 20 carbon atoms, and heteroatoms selected from the group consisting of oxygen, nitrogen, phosphorus and combinations thereof.

11. The method of claim 8 where the secondary amine has from 2 to 20 carbon atoms, may be linear, branched or cyclic and may be substituted with alkyl groups, aryl groups, alkylaryl groups, and aryl groups substituted with alkoxy groups.

12. The method of claim 8 where the reaction conditions comprise a temperature ranging from about ambient to about 120° C., and a pressure ranging from about ambient to that required to keep the reactants and solvents in the liquid phase.

* * * * *